United States Patent [19]
Kurdi-Haidar et al.

[11] Patent Number: 5,928,926
[45] Date of Patent: Jul. 27, 1999

[54] ISOLATION AND CLONING OF THE HUMAN ARSA-I GENE AND USES THEREOF

[75] Inventors: Buran Kurdi-Haidar, San Diego; Stephen B. Howell, Del Mar; Robert E. Enns, Solana Beach, all of Calif.; Peter Naredi, Varberg, Sweden

[73] Assignee: Research Development Foundation, Carson City, Nev.

[21] Appl. No.: 08/674,149

[22] Filed: Jul. 1, 1996

[51] Int. Cl.$^6$ .............................. C12N 9/14; C12N 1/20; C12N 15/00; C07H 21/04
[52] U.S. Cl. ................. 435/195; 435/252.3; 435/252.33; 435/320.1; 435/348; 435/325; 536/23.2
[58] Field of Search ................... 435/195, 252.3, 435/252.33, 348, 320.1, 325, 369; 536/23.2

[56] References Cited

PUBLICATIONS

Hillier et al. EST–STS database, Jun. 23, 1995, accesssion H08524.
Silver et al. (1988) Ann. Rev. Microbiol. 42, 717–743.

Primary Examiner—Keith D. Hendricks
Assistant Examiner—Elizabeth Slobodyansky
Attorney, Agent, or Firm—Benjamin Aaron Adler

[57] ABSTRACT

The present invention provides DNA encoding a human ARSA-I protein selected from the group consisting of: (a) isolated DNA which encodes a human ARSA-I protein; (b) isolated DNA which hybridizes to isolated DNA of (a) above and which encodes a human ARSA-I protein; and (c) isolated DNA differing from the isolated DNAs of (a) and (b) above in codon sequence due to the degeneracy of the genetic code, and which encodes a human ARSA-I protein. Also provided are pharmaceutical compositions comprising human human ARSA-I protein and a pharmaceutically acceptable carrier and host cells transfected with the vector of the present invention said vector expressing a human ARSA-I protein.

7 Claims, 8 Drawing Sheets

ISOLATION AND CLONING OF THE HUMAN ARSA-I GENE AND USES THEREOF

BACKGROUND OF THE INVENTION

1. Field of the Invention

The present invention relates generally to the fields of molecular toxicology, biochemistry and molecular biology. More specifically, the present invention relates to the isolation and cloning of the human ARSA-I gene.

2. Description of the Related Art

Little is known about mammalian detoxification systems involved with environmental heavy metal salt toxins. Some chemotherapeutic drugs are heavy metal-based and the development of resistance to such drugs occurs frequently during treatment and constitutes a major obstacle to the cure of even sensitive tumors. Resistance is thought to be due to the selection for and overgrowth of drug-resistant cells that arise through spontaneous somatic mutation. Biochemical studies have not succeeded in conclusively identifying the basis of resistance, but they have defined several mechanisms which can contribute to resistance. Platinum drugs do not participate in the multidrug resistance phenotype conferred by either the mdrl (P-glycoprotein) or M R P genes and only the ATP-dependent glutathione GS-X pump is known to modulate resistance to cisplatin.

Several transport-protein complexes that mediate the detoxification of heavy metal salts have been identified in bacteria and yeast, and appear to be structurally and functionally conserved throughout evolution. Resistance to arsenite, antimonite, tellurite, and arsenate in *E. coli.* and *S. aureus* is mediated by the plasmid-borne ars operon whose gene products together form an ATP-dependent pump that extrudes oxyanions and results in decreased uptake of these metalloid compounds.

Heavy metal salts are toxic to many types of organisms, and are important industrial toxins for man. Resistance to heavy metal salts in bacteria is mediated by specific plasmid-borne multicomponent ATP-dependent efflux systems (1,2). In *E. coli*, resistance to arsenite, arsenate and antimonite is mediated by the well-characterized ars operon (3) that contains two regulatory (arsR and arsD) and three structural genes (arsA, B and C) (2,4).

The gene arsA codes for an oxyanion-dependent ATPase that associates with the product of the arsB gene which is a putative channel-forming transmembrane protein. The ATP-binding cassette (ABC) of the arsA protein belongs to a superfamily of genes with a modified NTP-binding motif that is distinct from that present in other ATPases including the cation-translocating transporters (5,6). The arsA gene codes for a 583 amino acid (63 kDa) catalytic subunit with two ATP-binding cassette domains, whereas the arsB gene codes for a 429 amino acid (45.5 kDa) inner membrane protein with 12 transmembrane spanning domains that is postulated to serve both as the anion channel and an anchor for the ArsA protein (7). Together these two proteins transport arsenite and antimonite out of the cell. The arsC gene codes for a 141 amino acid (16 kDa) reductase capable of utilizing GSH as a cofactor to reduce arsenate ($As^{+5}$) to arsenite ($As^{+3}$), thus making it a substrate for ars transport system (8).

The prior art is deficient in the lack of the isolation and cloning of the human ARSA-I gene. The present invention fulfills this longstanding need and desire in the art.

SUMMARY OF THE INVENTION

Arsenite is an industrial and environmental toxin whose resistance in bacteria is mediated by an efflux pump composed of the arsA and arsB gene products. The present invention discloses the isolation and cloning of the human homolog of the bacterial arsA (hARSA-I), one of two closely related human genes. The hARSA-I gene is a widely expressed member of the ATPase superfamily with no transmembrane domain. Overexpression of the hARSA-I gene in the embryonal human kidney cell line 293 produced resistance to the oxyanion arsenite and to the cations cadmium and nickel indicative of a role for hARSA-I as a determinant of the human toxicology of heavy metal salts.

In one embodiment of the present invention, there is provided DNA encoding a human ARSA-I protein selected from the group consisting of: (a) isolated DNA which encodes a human ARSA-I protein; (b) isolated DNA which hybridizes to isolated DNA of (a) above and which encodes a human ARSA-I protein; and (c) isolated DNA differing from the isolated DNAs of (a) and (b) above in codon sequence due to the degeneracy of the genetic code, and which encodes a human ARSA-I protein.

In another embodiment of the present invention, there is provided a pharmaceutical composition, comprising human ARSA-I protein and a pharmaceutically acceptable carrier or excipient.

In still yet another embodiment of the present invention, there is provided a host cell transfected with the vector of the present invention, said vector expressing a human ARSA-I protein.

In another embodiment of the present invention, there is provided an isolated and purified human ARSA-I protein coded for by DNA selected from the group consisting of: (a) isolated DNA which encodes a human ARSA-I protein; (b) isolated DNA which hybridizes to isolated DNA of (a) above and which encodes a human ARSA-I protein; and (c) isolated DNA differing from the isolated DNAs of (a) and (b) above in codon sequence due to the degeneracy of the genetic code and which encodes a human ARSA-I protein.

In another embodiment of the present invention, there is provided DNA sequences encoding a human ARSA-I protein having the sequence shown in SEQ ID NO. 2.

In another embodiment of the present invention, there is provided the DNA which encodes a human ARSA-I protein, wherein said DNA has the sequence shown in SEQ ID NO. 1.

In another embodiment of the present invention, there is provided a vector comprising a DNA sequence which encodes a human ARSA-I protein and said vector is capable of replication in a host which comprises, in operable linkage: a) an origin of replication; b) a promoter; and c) a DNA sequence coding for said protein.

In another embodiment of the present invention, there is provided a host transformed with a recombinant DNA molecule, wherein said recombinant DNA molecule comprises a DNA sequence having the sequence of SEQ ID No. 1.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A and 1B-1 and 1B-2 show the structure of the hARSA-I gene and the strategy used for its cloning.

FIG. 1B shows the nucleotide and predicted amino acid sequences of hARSA-I (H) and its alignment with the C. elegans hypothetical arsA gene product (C). The potential poly(A) signal is underlined. Identical amino acids and conservative changes are indicated by (:) and (.), respectively.

FIG. 2A shows the northern analysis of poly(A)+RNA obtained from the human tissues shown above the lanes (21). Northern analysis was performed using a commercially obtained blot (Clontech, Palo Alto, Calif.). Each lane contained 2 mg of poly(A)+ RNA. Southern blot analysis was carried out using 10 mg of restriction enzyme-digested human genomic DNA obtained from human ovarian carcinoma 2008 cells.

FIG. 2B shows the southern analysis of human genomic DNA from human ovarian carcinoma 2008 cells digested with EcoR I and Hind III. Identical patterns of hybridization were obtained for the Northern and Southern analyses using the full length cDNA as a probe.

(FIG. 4A) Sodium arsenite ($Na_2AsO_3$), (FIG. 4B) cadmium chloride ($CdCl_2$), (FIG. 4C) nickel chloride ($NiCl_2$), and (FIG. 4D) zinc chloride ($ZnCl_2$). The calculated $IC_{50}$ values are depicted below the graphs which represent results of six independent assays each carried out in triplicate. P values were determined using the two-sided non-paired t-test.

DETAILED DESCRIPTION OF THE INVENTION

Figure 1A:
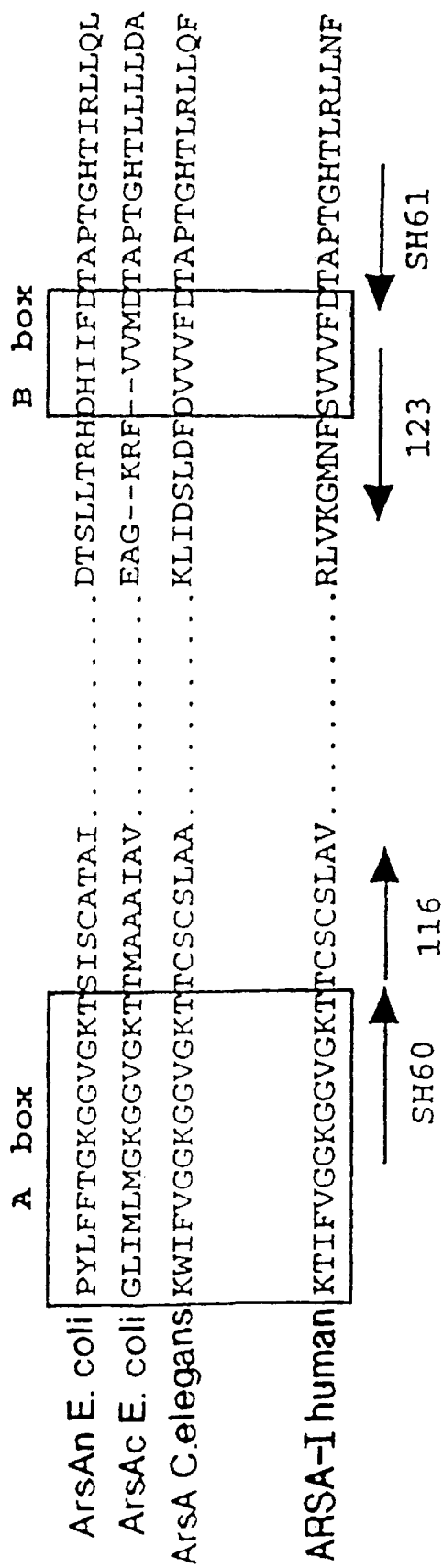
FIG. 1A shows the alignment of highly conserved amino acids within the ATP-binding cassette region of ArsA proteins. Labeled arrows indicate the location of motifs used to generate PCR primers (20). Degenerate primers matching conserved amino acid motifs were designed. SH60 is a degenerate 1024mer (5'-GGNAARGGNGGNGTNGG(G,C)AAAAC-3') and SH61 a degenerate 512mer (5'-GTRTGNCCNGTNGG(A,T)GTATC-3'). An random hexamer-primed cDNA library prepared from human ovarian carcinoma 2008 cells was amplified using Taq DNA polymerase (Boehringer Mannhein) and a total of 40 cycles with a temperature profile of 30 seconds at 94° C., 30 seconds at 50° C., and 60 seconds at 72° C. Amplification with primers 116 and 123 that match the nucleotide sequence of the ENA fragment: 116, 5'-CCACCTGCAGCTGCSGCCTGG-3'; 123,5'-CCACCACCGAGAAGTTCATGCCC-3' was carried out with an annealing temperature of 63° C. due to the their high G+C content. The conserved distinctive motifs shared by members of the ars superfamily and identified by Koonin et al. (5) as boxes A and B separated by 114 amino acids (dotted line) are shown.

Three heavy metal transporter genes have been identified in mammlian cells (6,9,10), two of which are P-type ATPases that appear to be involved in diseases of copper metabolism including the fatal X-linked Menkes disease (11) and the autosomal recessive Wilson's disease (9), and the third of which is a zinc ion transporter (10). To identify and characterize novel drug resistance genes, the present invention cloned a human arsA homolog. The C. elegans genomic sequencing project (12) identified two sequences with homology to the bacterial arsA gene. One of these, the hypothetical C. elegans arsA homolog, codes for a 342 amino acid protein with a single ATP-binding cassette domain (5), and the other is a short sequence that shares 80% sequence homology with the former. Previous alignment of the E. coli arsA with the C. elegans arsA (5) had revealed the presence of three conserved amino acid motifs designated the A, A', and B boxes within the ATP-binding cassette domain of both proteins that are also shared by other members of this superfamily.

The present invention identified and cloned the cDNA of a novel human gene (hARSA-I), the homolog of the E. coli. arsA gene that mediates resistance to arsenite. Furthermore, the present invention demonstrated that over-expression of hARSA-I gene in human ovarian carcinoma and transformed primary human embryonal kidney cells mediates resistance to arsenite, cadmium and nickel.

The identification and cloning of a novel gene that mediates heavy metal salt resistance will aid in resolving the problem of failure of tumors to respond to drug treatment in multiple ways. The hARSA-I gene is a previously undescribed gene which plays an important role in the understanding and management of drug resistance in clinical situations. Understanding the biological role of the hARSA-I gene in resistance development impacts medical treatment in several ways. For example, the teaching of the present invention permits the development of more effective tumor treatment measures in the form of concomitant administration of factors that will enhance tumor sensitivity thereby offsetting the emergence of resistance. Secondly, the teachings of the present invention provide a prognostic or predictive tool for effectiveness of tumor treatment, thereby reducing both the human and economic costs of cancer management. This prognostic or predictive tool is feasible to a person having ordinary skill in this art following the analysis of the molecular mechanisms underlying hARSA-I mediated drug resistance in clinical samples.

The present invention provides the sequence for the full-length hARSA-I cDNA and further demonstrated that overexpression of this gene does in fact produce a change in the phenotype of the cell, in this case producing resistance to arsenite, cadmium and nickel. The human ARSA-I gene may mediate resistance to a variety of other heavy metals.

The knowledge of this sequence of the novel gene of the present invention can be used as the basis for the development of a diagnostic and therapeutic strategies relevant to the treatment of cancer patients and to the broad field of environmental contamination by heavy metals. Heavy metals are major industrial toxins, and the protein product of the hARSA-I gene may play a role in the human toxicology of these metals. Applications include but are not limited to the following: (a) predicting the likely effectiveness of cancer drugs containing heavy metals (e.g., cisplatin, carboplatin), whose uptake into cells proves to be influenced by the presence of a functional hARSA-I protein leading to efficient intracellular delivery, and to guide the pharmaceutical industry in identification of analogs and novel drugs whose delivery is enhanced or conversely unaffected by the presence of the hARSA-I protein; (b) predicting the likely response of a given patient's tumor to cancer drugs containing heavy metals (e.g., cisplatin, carboplatin) if the level of expression of the hARSA-I in cells was found to correlate with the response to treatment; (c) identifying workers at high risk for the development of medical problems as a result of workplace exprosure to heavy metals or heavy metal-containing toxins once variation in the hARSA-I level in cirtical body tissues between individuals is determined (individuals may vary in their tolerance to heavy metal exposure); (d) engineering of organisms (e.g., yeast) that overproduces hARSA-I in a manner that allows such cells to take up and can concentrate heavy metals toxins and thus remove them from the environment.

The hARSA-I gene is a novel human gene whose product mediates resistance to multiple heavy metals including several environmental chemical toxins and potentially to related chemotherapeutic drugs. Only three transporters of specific heavy metals have been identified in mammalian cells each conferring resistance to a specific heavy metal, including: 1) a zinc transporter in rat liver; 2) a human P-type ATPase copper transporter involved in the fatal X-linked human Menkes disease; and 3) a second human copper transporter responsible for the autosomal recessive Wilson's disease. On the other hand, known multidrug resistance genes such as the mdr-1 (P-glycoprotein) and MRP are not involved with resistance to heavy metal chemotherapeutic drugs.

The hARSA-I cDNA is 1216 base pairs long and consists of 993 base pairs of coding sequence encoding for a 332 amino acid protein and a 215 base pairs 3' untranslated region. The hARSA-I protein contains a single ATP-binding cassette and no transmembrane domain. The availability of the hARSA-I gene opens the way for a number studies that can lead to various applications. For example, if the hARSA-I gene underlies a specific human genetic disease, the cDNA would be the basis for a diagnostic predictive test.

If hARSA-I gene expression is regulated by heavy metals, it could be used as the basis for an indicator test of environmental heavy metal contamination. If the hARSA-I gene is responsible for tumor resistance to heavy metal-based chemotherapeutic drugs, it could serve as the basis for a predictive test for likelihood of response to therapy, as well as a prognosis test for drug-resistant tumors.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomeclature, *J Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an automous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in tis either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human ARSA-I protein of the present invention can be used to transform a host using any of the techniques commonly known to those of ordinary skill in the art. Especially preferred is the use of a vector containing coding sequences for the gene which encodes a human ARSA-I protein of the present invention for purposes of prokaryote transformation.

Prokaryotic hosts may include *E. coli, S. tymphimurium, Serratia marcescens* and *Bacillus subtilis*. Eukaryotic hosts may include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The present invention comprises a vector comprising a DNA sequence coding for a which encodes a human ARSA-I protein and said vector is capable of replication in a host which comprises, in operable linkage: a) an origin of replication; b) a promoter; and c) a DNA sequence coding for said protein. Preferably, the vector of the present invention contains the DNA sequence shown in SEQ ID No. 1.

The present invention also comprises a host transformed with a recombinant DNA molecule, wherein said recombinant DNA molecule comprises a DNA sequence having the sequence of SEQ ID No. 1. A representative example of a host which may be transformed using the teachings herein is *E. coli*. An *E. coli* host transfected with a plasmid designated pKhARSA-I containing the recombinant DNA of the present was deposited with the American Type Culture Collection as Accession number ATCC 97620 on Jun. 20, 1996.

The following examples are given for the purpose of illustrating various embodiments of the invention and are not meant to limit the present invention in any fashion.

EXAMPLE 1

Synthesis Of Oligonucleotide Primers

Degenerate oligonucleotide primers were synthesized corresponding to two conserved primary amino acid sequence motifs (SH60 and SH61 in FIG. 1A) and amplified a 400 base pairs PCR product from a human cDNA library generated with random hexamer primers from the human ovarian carcinoma 2008 cells. The sequence of this fragment confirmed that it was a portion of a human gene which is a member of the arsA superfamily with a predicted amino acid primary sequence sharing 49% homology with the hypothetical *C. elegans* ArsA ATP-binding cassette domain (FIG. 1B).

Figure 1B:
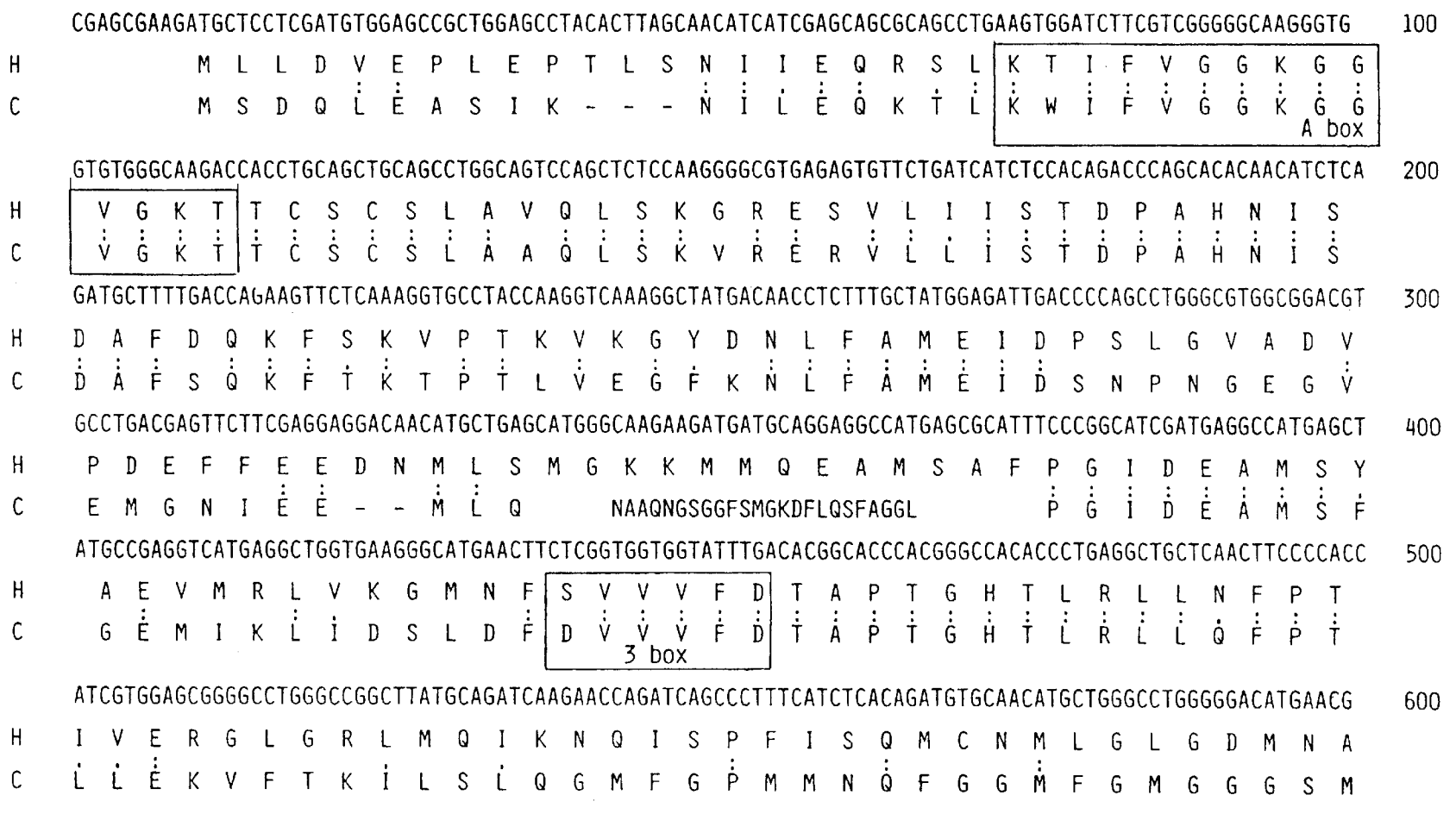
Figure 1B:
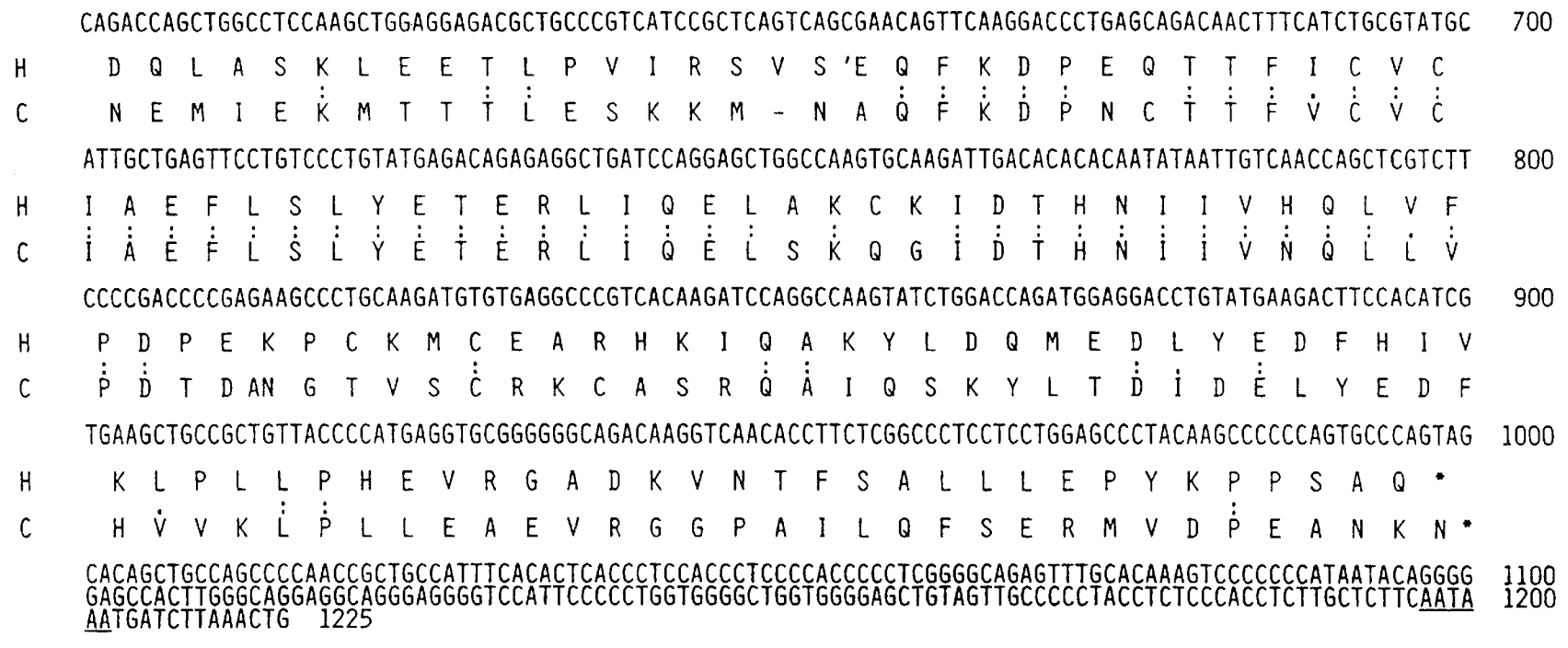
Figure 2A:
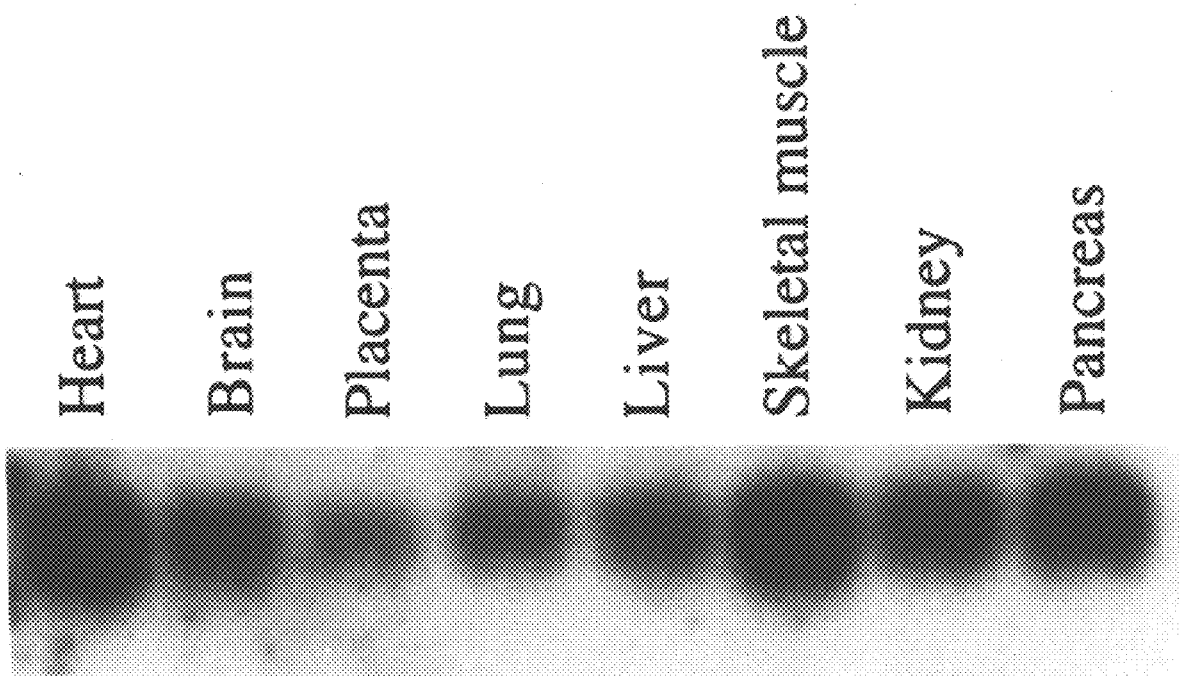
FIGS. 2A and 2B show the northern and southern blot analysis using the ENA fragment.

A human-specific fragment (designated as the ENA fragment) was amplified using nested primers (116 and 123 in FIG. 1A). Both the cDNA and human genomic DNA amplified the same product indicating that the ATP-binding cassette was present within a single exon. The size of the RNA message was estimated by Northern blot analysis of poly(A)+ RNA from several human tissues using the ENA fragment as probe. All examined tissues expressed a 1.2-kb transcript (FIG. 2A); mRNA levels were highest in cardiac and skeletal muscle.

EXAMPLE 2

Cloning of the hARSA-I cDNA

Cloning of the hARSA-I cDNA, its 5' end, and construction of its full length cDNA was successfully carried out (13). A Uni-Zap™ human liver cDNA library (Stratagene, La Jolla, Calif.) was screened using the ENA fragment as probe and a 1207-bp ENA-hybridizing cDNA was obtained. Sequencing indicated that this cDNA contained the 3' untranslated region and most of the coding sequence, but lacked the initiation codon at the 5' end.

The 5' end of the hARSA-I cDNA was obtained as an amplification product using two successive steps. During the first step, a vector-specific primer:
(B1, 5'-GGAAACAGCTATGACCATGATTACG-3')

and a cDNA-specific primer:
(B12, 5'-CACATCTGTGAGATGAAAGGG-3') produced an anticipated smear. The second step of amplification with primers B1 and B23 (B23, 5'-GAACACTCTCACGCCCCT-3') amplified the missing 5' end of the hARSA-I cDNA which contained the translation initiation ATG preceded by a potential Kozak sequence.

EXAMPLE 3

Sequencing of the full length hARSA-I cDNA

The full-length hARSA-I cDNA was reconstructed by PCR amplification of a mixture of the 5' end PCR fragment and the overlapping partial hARSA-I using primers derived from the non-overlapping ends, B24 (5'-CGAGCGAAGATGCTCCTC-3') spanning the initiation ATG and B7 (5'-GATCATTTATTGAAGAGCAAGAGG-3') derived from the 3' untranslated region. All PCR amplifications were carried out in the presence of the Taq polymerase extender (Stratagene, La Jolla, Calif.) using the manufacture's instructions and a total of 32 cycles with a temperature profile of 30 seconds at 93° C., 30 seconds at 56° C., and 60° C. at 72° C. Sequencing was carried out using the fmol™ DNA sequencing system (Promega, Wisconsin).

Sequencing of the full length cDNA indicated that it encodes a protein composed of 332 amino acids with a single ATP-binding cassette domain (FIG. 1B) which is 52% homologous in amino acid sequence to the hypothetical *C. elegans* ArsA and includes both an N-terminal ATP-binding cassette domain and a C-terminal domain of unknown function (FIG. 1B).

Figure 2B:
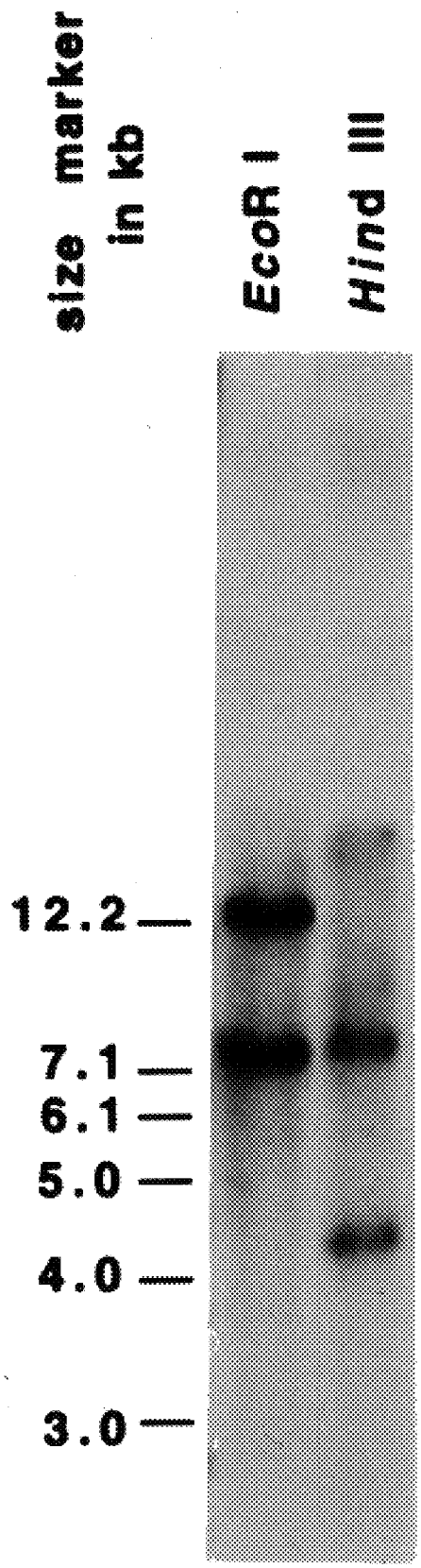

Southern blot analysis of human genomic DNA digested with enzymes absent from the ENA fragment revealed the presence of two hybridizing genomic bands (FIG. 2B) suggesting the presence of two hARSA genes, reminiscent of the two homologous sequences found in *C. elegans* (12). Unlike the bacterial arsA gene, which encodes a protein with 2 ATP-binding cassette domains believed to have arisen from a duplication event (3), both human and *C. elegans* ArsA proteins are approximately half the size of the bacterial ArsA and contain a single ATP-binding cassette domain. It is likely that the duplication event in eukaryotes resulted in two independent genes rather than a single fusion protein. In view of these findings, the currently described hARSA gene was designated hARSA-I.

EXAMPLE 4

Treatment with hARSA-specific rabbit antibody

To determine whether the two hybridizing bands represent different functional genes encoding homologous isoforms, a hARSA-specific rabbit antibody was prepared. A glutathione-S-transferase (GST)-hARSA-I fusion protein was produced in *E. coli* (14) and the affinity purified fusion protein was used to immunize rabbits. A prokaryotic expression vector was constructed by inserting the full length cDNA in frame into the BamH I site within vector pGEX-3X (Pharmacia Biotech, Uppsala, Sweden) producing a glutathione-S-transferase (GST)/hARSA-I fusion protein separated by a Factor Xa cleavage site. The proper frame of the inserted hARSA-I was confirmed by direct sequencing of pGEX-3X-hARSA-I. The recombinant GST/hARSA-I fusion protein was overproduced in XL-1 blue cells (Stratagene, La Jolla, Calif.) and purified as described in (D. B. Smith, L. M. Corcoran, in *Curr Protocols Mol Biol*, F. M. Ausubel, et al., Eds. (John Wiley & Sons, Inc, Massachusetts, 1992), vol. 2, pp. 16.7.1–16.7.8.). hARSA-I-specific immune serum was commercially raised in rabbits (R. Seargent, Ramona, Calif.) injected with 1 mg of the GST-hARSA-I fusion protein.

Western blot analysis was carried out using established techniques such as those described by H. Towbin et al., *J Clin Chem Clin Biochem* 27, 495–501). Proteins were electroblotted onto a PVDF membrane (Immobilon P, Millipore, Bedford Mass.) and signal detection was carried out using an enhanced chemiluminescence system (Amersham, Arlington Heights, Ill.).

The hARSA-I-specific immune serum was used to analyze cellular lysates of adenovirus (AD5)-transformed human embryonal kidney cell 293 cells by Western blot. Two cross-reacting proteins of 37 and 42 kDa were identified (FIG. 3, lanes 1 and 2), providing further evidence for the presence of 2 hARSA isoforms. Identical results were obtained with human ovarian carcinoma 2008 cells (data not shown). Although both Southern and Western blot analysis indicated the existence of two isoforms, only one transcript was identified by Northern analysis. This apparent discrepancy is likely to be due to the fact that the size difference between the two transcripts is too small to be resolved under the conditions used for the Northern blot, and it is likely that the hybridizing band is composed of overlapping hARSA-I and hARSA-II transcripts.

In order to identify phenotypic changes mediated by hARSA-I, 293 cells were engineered to overexpress hARSA-I by constructing a eukaryotic expression vector pRc/CMV-hARSA-I which contains neo as a selectable marker (15). A eukaryotic expression vector was constructed by inserting the hARSA-I cDNA full-length kinased PCR fragment into the filled-in Xba I site in the eukaryotic expression vector pRc/CMV (Invitrogen, San Diego, Calif.) under the control of the human cytomegalovirus (CMV) immediate early gene enhancer/promotor sequences to produce the expression plasmid pRc/CMV-hARSA-I. This vector also contained the neomycin phosphotransferase gene under the control of the RSV-long terminal repeat (LTR). Transfection of 293 cells was carried out by lipofection as is well known in the art. See, e.g., P. Felgner, et al., *Proc Natl Acad Sci USA* 84: 7413–7417 (1987) and transfected cells were selected 48 hours post lipofection in 400 mg/ml G418.

Figure 3:
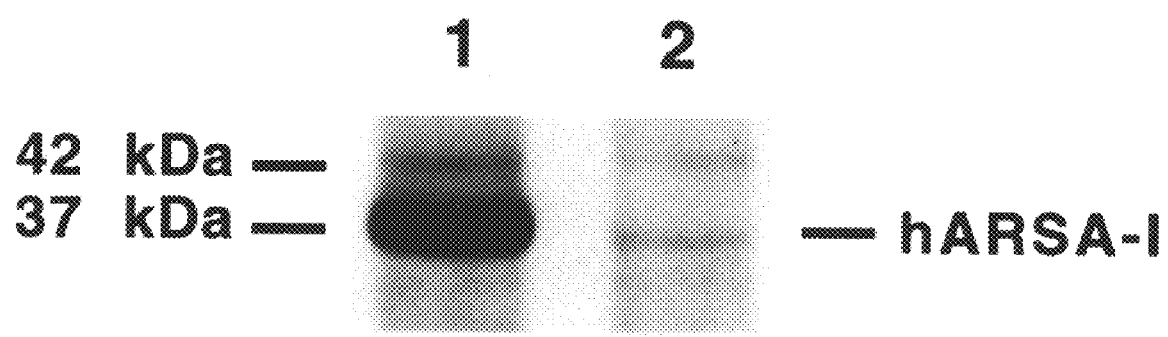
FIG. 3 shows a western blot analysis of 293 and 293/hARSA-I human embryonal kidney cells. Cellular lysates (50 mg) from 293 cells (lane 2) and 293/hARSA-I cells (lane 1) were separated using 10% sodium dodecyl sulfate-polyacrylamide gel electrophoresis (SDS-PAGE) and transferred to a PVDF membrane and were incubated with rabbit hARSA-I polyclonal antibody (14), detected using a peroxidase-conjugated goat anti-rabbit antibody and developed using enhanced chemiluminescense (22).

A population of G418-resistant cells (293/hARSA-I) was generated from pRc/CMV-hARSA-I-transfected cells (15) and overproduction of hARSA-I in this population was confirmed by Western analysis using the hARSA-I-specific rabbit polyclonal antibody (FIG. 3, lane 1). While increased levels of the 37 kDa protein were observed in 293/hARSA-I cells, no difference in the level of the 42 kDa cross-reacting protein was found, indicating that the hARSA-I gene encodes for the 37 kDa hARSA-I isoform.

EXAMPLE 5 hARSA-I Expression and Resistance to Arsenite

The ability of hARSA-I expression to mediate resistance to arsenite was investigated by measuring the inhibitory effect of a 1 hour exposure to increasing concentrations of arsenite on the growth of 293 and 293/hARSA-I cells using the sulforhodamine B assay (16,17). The sulphorhodamine B assay was carried out by seeding 6,000 cells/well in 96-well plates for 24 hours. Control plates were fixed at this time 0 ($T_0$) and test wells were treated for one hour with the appropriate heavy metal salt, then fixed after an 48 hours of growth in 50% (w/v) trichloroacetic acid. Staining of cellular proteins with sulforhodamine B was spectrophotometrically measured at 515 nm and the relative growth (R) was calculated. If absorption at T>$T_0$, R=(T–$T_0$)/(C–$T_0$); if T<$T_0$, R=(T–$T_0$)/$T_0$ (A. Monks, et al.,*J Natl Cancer Inst* 83, 757–765 (1991) with T being the absorption 72 hours after drug treatment, C the absorption at time 72 hours in controls, and To the absorption immediately before drug treatment. $IC_{50}$ values were estimated by linear interpolation at an R value of 0.5.

The 293/hARSA-I cells were 1.7-fold resistant to arsenite based on the ratio of the $IC_{50}$ concentrations (FIG. 6A). The data presented in FIG. 4B and C show that the 293/hARSA-I cells were also 1.5-fold resistant to cadmium chloride and a 1.6-fold resistant to nickel chloride. No difference in sensitivity to zinc chloride was observed (FIG. 4D). Thus, the present invention demonstrates that overexpression of hARSA-I mediates resistance to two different cations in addition to the oxyanion ($As^{+3}$). Furthermore, the present invention demonstrates that although both hARSA isoforms are expressed in human cells, overexpression of hARSA-I alone is sufficient to produce resistance to these heavy metal salts.

The present invention demonstrates that the hARSA-I gene is a component of a human heavy metal transport system. This system is likely to be composed of multiple proteins including a second isoform, hARSA-II, and at least one as yet unidentified transmembrane protein, homologous to bacterial arsB, that functions to either transport arsenite out of the cell or sequester it within the cell. The hARSA-I-mediated modulation of resistance to anionic as well as cationic heavy metals could be a reflection of the low substrate specificity of the human arsenite pump. However, this is an unlikely possibility because known ATP-binding cassette transporters are most often specific for single substrates or groups of closely-related substrates (18). On the other hand, modulator proteins analogous to the bacterial arsC could exist in human cells and may be able to interact with hARSA-I extending the specificity of the arsenite pump to include cationic heavy metals.

Recent findings indicate that some ATP-binding cassette transporters regulate the activity of heterologous transporters (reviewed in 18). This provides an alternative explanation for the cross-resistance observed between arsenite, cadmium and nickel.

First, binding of different heavy metals to the catalytic subunit could result in association of hARSA-I with different transmembrane channel proteins, an interaction that may dictate the heavy metal specificity. Second, overexpression of hARSA-I may activate independent heterologous cadmium and nickel channels indirectly through interaction with an intermediate proteins analogous to the ankyirin/spectrin-mediated interaction between the glucose transporter and the band three anion exchanger $Na^+/K^+$-ATPase (Mills, et al., *Curr Opin Nephrol Hyperten* 3, 529–534 (1994). Studies identifying the cellular proteins with which hARSA-I interacts in the absence and presence of heavy metal salts will enhance understanding of the mechanisms of this resistance phenotype.

The following references were cited herein.

1. Silver et al., *Environ Health Perspect* 102(3), 107–113 (1994).
2. P. Kaur, et al., *Plasmid* 27, 29–40 (1992).
3. B. P. Rosen, et al., *Biochim Biophys Acta* 1018, 203–205 (1990).
4. S. Broer, et al., *J Bacteriol* 175, 3480–3485 (1993).
5. E. V. Koonin, *J Mol Biol* 229, 1165–1174 (1993).
6. S. Silver, et al., *Mol Microbiol* 8, 637–642 (1993).
7. B. P. Rosen, et al., *Arch Biochem Biophys* 284, 381–385 (1991).
8. K. L. Oden, et al., *Mol Microbiol* 12, 301–306 (1994).
9. K. Petrukhin, et al., *Hum Mol Genet* 3, 1647–1656 (1994).
10. R. D. Palmiter, S. D. Findley, *EMBO J* 14, 639–649 (1995).
11. J. F. Mercer, et al., *Nature Genet* 3, 20–25 (1993).
12. J. Sulston, et al., *Nature* 356, 37–41 (1992).
22. P. Lorimier, et al., *J Histochem Immunohistochem* 41, 1591–1597 (1993).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention.

Changes therein and other uses will occur to those skilled in the art which are encompassed within the spirit of the invention as defined by the scope of the claims.

What is claimed is:

1. DNA encoding a human ARSA-I protein selected from the group consisting of:
   (a) isolated DNA which encodes a human ARSA-I protein; and
   (b) isolated DNA differing from the isolated DNA of (a) above in codon sequence due to the degeneracy of the genetic code, and which encodes a human ARSA-I protein.

2. The DNA of claim 1, wherein said human ARSA-I protein has the amino acid sequence shown in SEQ ID No. 2.

3. A vector comprising a DNA sequence which encodes a human ARSA-I protein and said vector is capable of replication in a host which comprises, in operable linkage: a) an origin of replication; b) a promoter; and c) a DNA sequence coding for said protein.

4. The vector of claim 3, wherein said DNA is the DNA shown in SEQ ID No. 1.

5. A host cell transfected with the vector of claim said vector expressing a human ARSA-I protein.

6. The host cell of claim wherein said cell is selected from group consisting of bacterial cells, mammalian cells and insect cells.

7. The host cell of claim wherein said bacterial cell is *E. coli*.

\* \* \* \* \*

UNITED STATES PATENT AND TRADEMARK OFFICE
CERTIFICATE OF CORRECTION

PATENT NO.   : 5,928,926
DATED        : July 27, 1999
INVENTOR(S)  : Buran Kurdi-Haidar, Stephen B. Howell, Robert E. Enns, and Peter Naredi It is certified that error appears in the above-identified patent and that said Letters Patent is hereby corrected as shown below:

Abstract,
Line 10, please delete the second word "human".

Figure 1B,
Sheet 2 of 8, where it has "3 box", it should read -- B box --.
Sheet 3 of 8, after the 56$^{th}$ letter which is C, there should be a letter -- I -- inserted, and goes on to read "GAACAGTTC...",.
Line 5, fifth letter from the end which reads as "H" should read -- N --.

Figure 4:
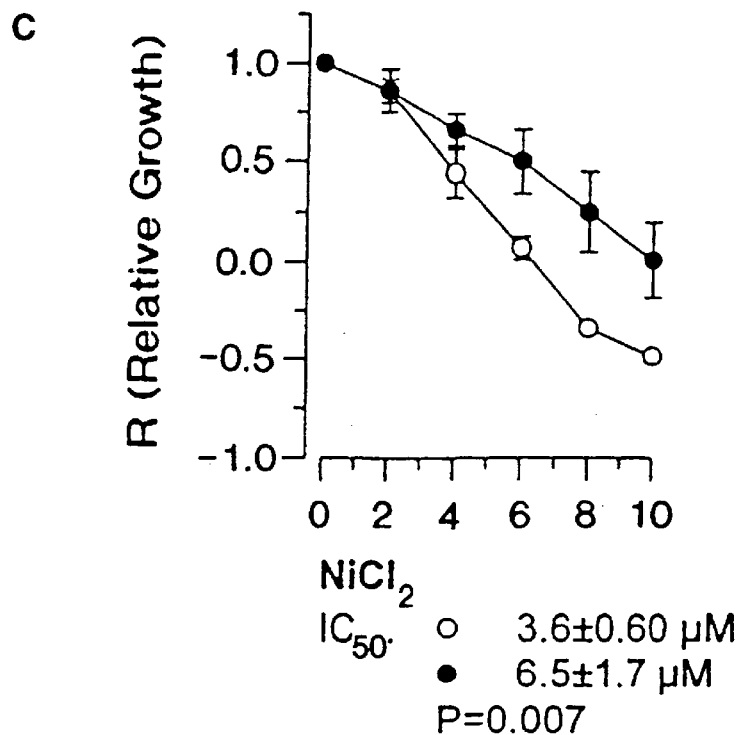
FIG. 4A–4D show the growth inhibition of 293/hARSA-I and 293 control cells in the presence of heavy metals as measured by the sulforhodamine B assay (16, 17). Open circles: 293/hARSA-I cells; closed circles: 293 control cells; R: relative growth (C. F. Higgins, Cell 82, 693–696 (1995) in the presence of the specified concentrations of heavy metals.
Figure 4:
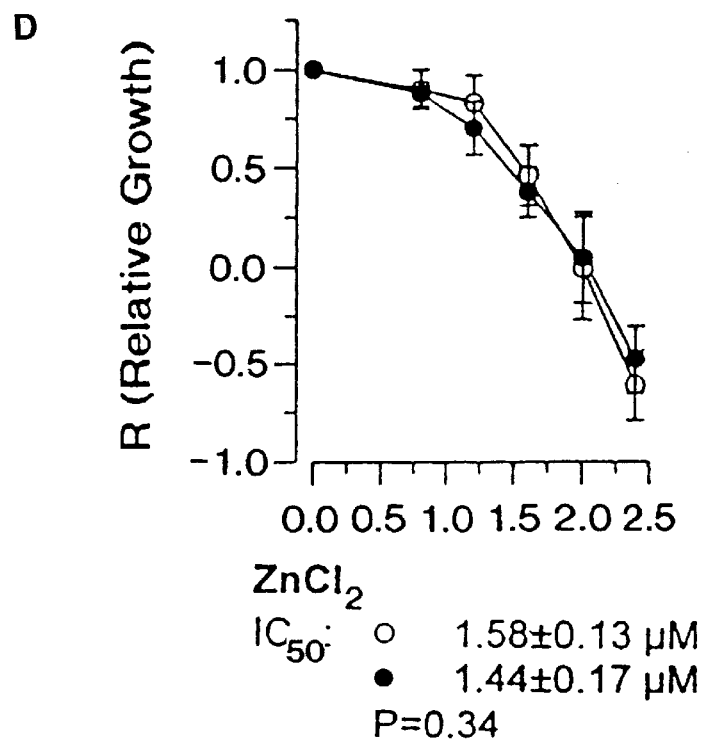
Figure 4:
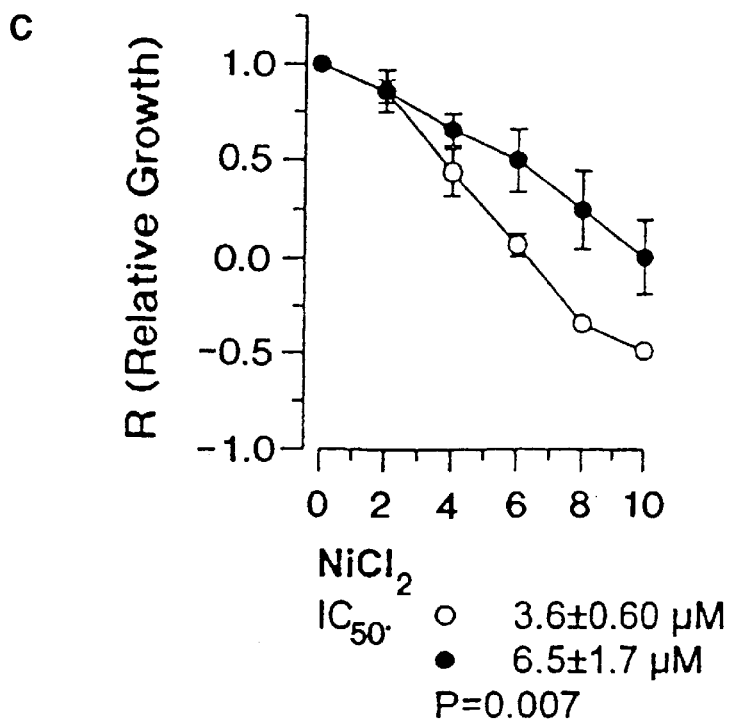
Figure 4:
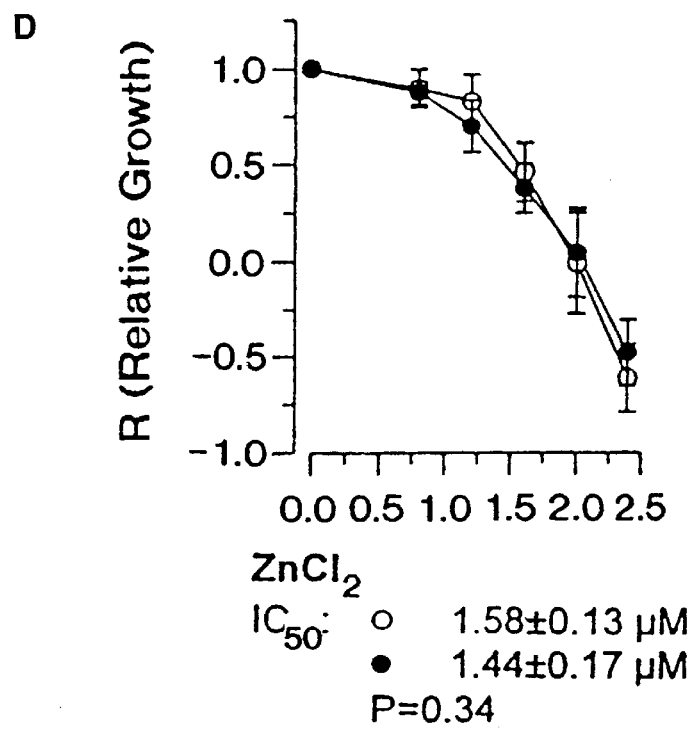

Figure 4,
Sheet 7 of 8, where the Figures read "C" and "D", they should read -- A -- and -- B --.

Column 3,
Line 15, "An" should read -- A --.

Column 4,
Line 10, "mammlian" should read -- mammalian --.
Line 64, please delete the word "a" between the words "of" and "diagnostic".

Column 5,
Line 15, "exprosure" should read -- exposure --.
Line 17, "cirtical" should read -- critical --.
Line 57, please insert closed quotations after the word "Manual".

Column 6,
Line 1, "acid" should read -- acids --.
Line 9, "nomeclature" should read -- nomenclature --.
Line 53, "tis" should read -- its --.

Column 8,
Line 15, please insert the word -- can -- between the words "or" and "hybrid-".
Line 52, please insert closed quotation marks after the word "heterologous".

Column 9,
Line 28, "quantitiy" should read -- quantity --.

Column 10,
Line 11, please delete the words "coding for a".
Line 23, please insert the word -- invention -- after the word "present".

UNITED STATES PATENT AND TRADEMARK OFFICE
CERTIFICATE OF CORRECTION

PATENT NO.    : 5,928,926
DATED         : July 27, 1999
INVENTOR(S)   : Buran Kurdi-Haidar, Stephen B. Howell, Robert E. Enns, and Peter Naredi It is certified that error appears in the above-identified patent and that said Letters Patent is hereby corrected as shown below:

Column 11,
Lines 18-19, "manufacture's" should read -- manufacturer's --.
Lines 20-21, "60° C." should read -- 60 seconds. --

Column 12,
Line 57, please delete the word "an".
Line 65, "To" should read -- $T_o$ --.

Column 13,
Line 4, please delete the word "a" at the end of the line.
Line 42, please delete the word "an".

Column 14,
Line 21, "10." should read -- 10. --.

Column 27,
Line 25, please insert the words -- and wherein said DNA has the sequence shown in SEQ ID No. 1 -- before the semi-colon.
Lines 33-34, please delete the words "sequence which encodes a human ARSA-I protein and" and replace it with -- of claim 1, wherein --.

UNITED STATES PATENT AND TRADEMARK OFFICE
CERTIFICATE OF CORRECTION

PATENT NO.   : 5,928,926
DATED        : July 27, 1999
INVENTOR(S)  : Buran Kurdo-Haidar, Stephen B. Howell, Robert E. Enns, and Peter Naredi It is certified that error appears in the above-identified patent and that said Letters Patent is hereby corrected as shown below:

Column 28,
Line 21, please insert the word -- cell -- between the words "host" and "which".
Line 22, please delete the word "a" after the "c)" and replace it with -- said --.
Lines 22-23, please delete the words "sequence coding for said protein".
Line 26, please insert the number -- 4. -- after the word "claim".
Lines 26-27, please delete the words "said vector expressing a human ARSA-I protein"/
Line 28, please insert the number -- 5. -- after the word "claim".
Line 31, please insert the number -- 6. -- after the world "claim".

Signed and Sealed this

Twentieth Day of November, 2001

Attest:

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 1225 base pairs
      (B) TYPE: nucleic acid
      (C) STRANDEDNESS: double-stranded
      (D) TOPOLOGY: unknown (ii) MOLECULE TYPE: cDNA (iii) HYPOTHETICAL: no (iv) ANTI-SENSE: no (v) SEQUENCE DESCRIPTION: SEQ ID NO:1:

CGAGCGAAGA TGCTCCTCGA TGTGGAGCCG CTGGAGCCTA CACTTAGCAA CATCATCGAG   60

```
CAGCGCAGCC TGAAGTGGAT CCTCGTCGGG GGCAAGGGTG GTGTGGGCAA GACCACCTGC      120

AGCTGCAGCC TGGCAGTCCA GCTCTCCAAG GGGCGTGAGA GTGTTCTGAT CATCTCCACA      180

GACCCAGCAC ACAACATCTC AGATGCTTTT GACCAGAAGT TCTCAAAGGT GCCTACCAAG      240

GTCAAAGGCT ATGACAACCT CTTTGCTATG GAGATTGACC CCAGCCTGGG CGTGGCGGAC      300

GTGCCTGACG AGTTCTTCGA GGAGGACAAC ATGCTGAGCA TGGGCAAGAA GATGATGCAG      360

GAGGCCATGA GCGCATTTCC CGGCATCGAT GAGGCCATGA GCTATGCCGA GGTCATGAGG      420

CTGGTGAAGG GCATGAACTT CTCGGTGGTG GTATTTGACA CGGCACCCAC GGGGCACACC      480

CTGAGGCTGC TCAACTTCCC CACCATCGTG GAGCGGGGCC TGGGCCGCCT TATGCAGATC      540

AAGAACCAGA TCAGCCCTTT CATCTCACAG ATGTGCAACA TGCTGGGCCT GGGGGACATG      600

AACGCAGACC AGCTGGCCTC CAACGTGGAG GAGACGCTGC CCGTCATCCG CTCAGTCAGC      660

GAACAGTTCA AGGACCCTGA GCAGACAACT TTCATCTGCG TATGCATTGC TGAGTTCCTG      720

TCCCTGTATG AGACAGAGAG GCTGATCCAG GAGCTGGCCA AGTGCAAGAT TGACACACAC      780

AATATAATTG TCAACCAGCT CGTCTTCCCC GACCCCGAGA AGCCCTGCAA GATGTGTGAG      840

GCCCGTCACA AGATCCAGGC CAAGTATCTG GACCAGATGG AGGACCTGTA TGAAGACTTC      900

CACATCGTGA AGCTGCCGCT GTTACCCCAT GAGGTGCGGG GGGCAGACAA GGTCAACACC      960

TTCTCGGCCC TCCTCCTGGA GCCCTACAAG CCCCCCAGTG CCCAGTAGCA CAGCTGCCAG      1020

CCCCAACCGC TGCCATTTCA CACTCACCCT CCACCCTCCC CACCCCCTCG GGCAGAGTT      1080

TGCACAAAGT CCCCCCCATA ATACAGGGGG AGCCACTTGG GCAGGAGGCA GGGAGGGGTC      1140

CATTCCCCCT GGTGGGGCTG GTGGGGAGCT GTAGTTGCCC CCTACCTCTC CCACCTCTTG      1200

CTCTTCAATA AATGATCTTA AACTG                                            1225
```

(2) INFORMATION FOR SEQ ID NO: 2:

(i) SEQUENCE CHARACTERISTICS:
        (A) LENGTH: 333
        (B) TYPE: amino acid
        (C) STRANDEDNESS:
        (D) TOPOLOGY: linear (ii) MOLECULE TYPE: Protein (iii) HYPOTHETICAL: No (iv) ANTI-SENSE: No (v) SEQUENCE DESCRIPTION: SEQ ID NO:2:

```
Met Leu Leu Leu Asp Val Glu Pro Leu Glu Pro Thr Leu Ser Asn
                5                  10                  15

Ile Ile Glu Gln Arg Ser Leu Lys Thr Ile Phe Val Gly Gly Lys
                20                 25                  30

Gly Gly Val Gly Lys Thr Thr Cys Ser Cys Ser Leu Ala Val Gln
                35                 40                  45

Leu Ser Lys Gly Arg Glu Ser Val Leu Ile Ile Ser Thr Asp Pro
                50                 55                  60

Ala His Asn Ile Ser Asp Ala Phe Asp Gln Lys Phe Ser Lys Val
                65                 70                  75

Pro Thr Lys Val Lys Gly Thr Asp Asn Leu Phe Ala Met Glu Ile
                80                 85                  90

Asp Pro Ser Leu Gly Val Ala Asp Val Pro Asp Glu Phe Phe Glu
                95                100                 105
```

```
Glu Asp Asn Met Leu Ser Met Gly Lys Lys Met Met Gln Glu Ala
            110                 115                 120

Met Ser Ala Phe Pro Gly Ile Asp Glu Ala Met Ser Tyr Ala Glu
            125                 130                 135

Val Met Arg Leu Val Lys Gly Met Asn Phe Ser Val Val Val Phe
            140                 145                 150

Asp Thr Ala Pro Thr Gly His Thr Leu Arg Leu Leu Asn Phe Pro
            155                 160                 165

Thr Ile Val Glu Arg Gly Leu Gly Arg Leu Met Gln Ile Lys Asn
            170                 175                 180

Gln Ile Ser Pro Phe Ile Ser Gln Met Cys Asn Met Leu Gly Leu
            185                 190                 195

Gly Asp Met Asn Ala Asp Gln Leu Ala Ser Lys Leu Glu Glu Thr
            200                 205                 210

Leu Pro Val Ile Arg Ser Val Ser Glu Gln Phe Lys Asp Pro Glu
            215                 220                 225

Gln Thr Thr Phe Ile Cys Val Cys Ile Ala Glu Phe Leu Ser Leu
            230                 235                 240

Tyr Glu Thr Glu Arg Leu Ile Gln Glu Leu Ala Lys Cys Lys Ile
            245                 250                 255

Asp Thr His Asn Ile Ile Val Asn Gln Leu Val Phe Thr Asp Pro
            260                 265                 270

Glu Lys Pro Cys Lys Met Cys Glu Ala Arg His Lys Ile Gln Ala
            275                 280                 285

Lys Tyr Leu Asp Gln Met Glu Asp Leu Tyr Glu Asp Phe His Ile
            290                 295                 300

Val Lys Leu Pro Leu Leu Pro His Glu Val Arg Gly Ala Asp Lys
            305                 310                 315

Val Asn Thr Phe Ser Ala Leu Leu Leu Glu Pro Tyr Lys Pro Pro
            320                 325                 330

Ser Ala Gln
      333

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: Yes (v) SEQUENCE DESCRIPTION: SEQ ID NO:3:

GGNAARGGNG GNGTNGGGCA AAAC                                          24

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no
```

(iv) ANTI-SENSE: Yes (v) SEQUENCE DESCRIPTION: SEQ ID NO:4:

GTRTGNCCNG TNGGTGTATC                                            20

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:5:

CCACCTGCAG CTGCSGCCTG G                                          21

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:6:

CCACCACCGA GAAGTTCATG CCC                                        23

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:7:

GGAAACAGCT ATGACCATGA TTACG                                      25

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:8:

CACATCTGTG AGATGAAAGG G                                               21

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:9:

GAACACTCTC ACGCCCCT                                                   18

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:10:

CGAGCGAAGA TGCTCCTC                                                   18

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: double-stranded
        (D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:11:

GATCATTTAT TGAAGAGCAA GAGG                                            24

(2) INFORMATION FOR SEQ ID NO: 12:

(i) SEQUENCE CHARACTERISTICS:
        (A) LENGTH: 338
        (B) TYPE: amino acid
        (C) STRANDEDNESS:
        (D) TOPOLOGY: linear (ii) MOLECULE TYPE: Protein (iii) HYPOTHETICAL: No (iv) ANTI-SENSE: No (v) SEQUENCE DESCRIPTION: SEQ ID NO:12:

Met Ser Asp Gln Leu Glu Ala Ser Ile Lys Asn Ile Leu Glu Gln
            5                  10                15

```
Lys Thr Leu Lys Trp Ile Phe Val Gly Gly Lys Gly Val Gly
                 20                  25                  30

Lys Thr Thr Cys Ser Cys Ser Leu Ala Ala Gln Leu Ser Lys Val
             35                  40                  45

Arg Glu Arg Val Leu Leu Ile Ser Thr Asp Pro Ala His Asn Ile
             50                  55                  60

Ser Asp Ala Phe Ser Lys Lys Phe Thr Lys Thr Pro Thr Leu Val
             65                  70                  75

Glu Gly Phe Lys Asn Leu Phe Ala Met Glu Ile Asp Ser Asn Pro
             80                  85                  90

Asn Gly Glu Gly Val Glu Met Gly Asn Ile Glu Glu Asn Leu Gln
             95                  100                 105

Asn Ala Ala Gln Asn Gly Ser Gly Gly Phe Ser Met Gly Lys Asp
             110                 115                 120

Phe Leu Gln Ser Phe Ala Gly Gly Leu Pro Gly Ile Asp Glu Ala
             125                 130                 135

Met Ser Phe Gly Glu Met Ile Lys Leu Ile Asp Ser Leu Asp Phe
             140                 145                 150

Asp Val Val Val Phe Asp Thr Ala Pro Thr Gly His Thr Leu Arg
             155                 160                 165

Leu Leu Gln Phe Pro Thr Leu Leu Glu Gln Val Phe Thr Lys Ile
             170                 175                 180

Leu Ser Leu Gln Gly Met Phe Gly Pro Met Met Asn Gln Phe Gly
             185                 190                 195

Gly Met Phe Gly Met Gly Gly Ser Met Asn Glu Met Ile Glu
             200                 205                 210

Lys Met Thr Thr Thr Leu Glu Ser Lys Lys Met Met Ala Lys Phe
             215                 220                 225

Lys Asp Pro Asn Cys Thr Thr Phe Val Cys Val Cys Ile Ala Glu
             230                 235                 240

Phe Leu Ser Leu Thr Glu Thr Glu Arg Leu Ile Gln Glu Leu Ser
             245                 250                 255

Lys Gln Gly Ile Asp Thr His Asn Ile Ile Val Asn Gln Leu Leu
             260                 265                 270

Phe Pro Asp Thr Asp Ala Gly Thr Val Ser Cys Arg Lys Cys Ala
             275                 280                 285

Ser Arg Gln Ala Ile Gln Ser Lys Thr Leu Thr Asp Ile Asp Glu
             290                 295                 300

Leu Thr Glu Asp Phe His Val Val Lys Leu Pro Leu Leu Glu Ala
             305                 310                 315

Glu Val Arg Gly Gly Pro Ala Ile Leu Gln Phe Ser Glu Arg Met
             320                 325                 330

Val Asp Pro Glu Ala Asn Lys Asn
                         338

(2) INFORMATION FOR SEQ ID NO: 13:

(i) SEQUENCE CHARACTERISTICS:
        (A) LENGTH: 49
        (B) TYPE: amino acid
        (C) STRANDEDNESS:
        (D) TOPOLOGY:   linear (ii) MOLECULE TYPE:  Protein (iii) HYPOTHETICAL: No
```

(iv) ANTI-SENSE: No (v) SEQUENCE DESCRIPTION: SEQ ID NO:13:

Pro Tyr Leu Phe Phe Thr Gly Lys Gly Val Gly Lys Thr Ser
                 5                  10                  15

Ile Ser Cys Ala Thr Ala Ile Asp Thr Ser Leu Leu Thr Arg His
                 20                  25                  30

Asp His Ile Ile Phe Asp Thr Ala Pro Thr Gly His Thr Ile Arg
                 35                  40                  45

Leu Leu Gln Leu
            49

(2) INFORMATION FOR SEQ ID NO: 14:

(i) SEQUENCE CHARACTERISTICS:
        (A) LENGTH: 45
        (B) TYPE: amino acid
        (C) STRANDEDNESS:
        (D) TOPOLOGY: linear (ii) MOLECULE TYPE: Protein (iii) HYPOTHETICAL: No (iv) ANTI-SENSE: No (v) SEQUENCE DESCRIPTION: SEQ ID NO:14:

Gly Leu Ile Met Leu Met Gly Lys Gly Val Gly Lys Thr Thr
                 5                  10                  15

Met Ala Ala Ala Ile Ala Val Glu Ala Gly Lys Arg Phe Val Val
                 20                  25                  30

Met Asp Thr Ala Pro Thr Gly His Thr Leu Leu Leu Asp Ala
                 35                  40                  45

(2) INFORMATION FOR SEQ ID NO: 15:

(i) SEQUENCE CHARACTERISTICS:
        (A) LENGTH: 49
        (B) TYPE: amino acid
        (C) STRANDEDNESS:
        (D) TOPOLOGY: linear (ii) MOLECULE TYPE: Protein (iii) HYPOTHETICAL: No (iv) ANTI-SENSE: No (v) SEQUENCE DESCRIPTION: SEQ ID NO:15:

Lys Trp Ile Phe Val Gly Gly Lys Gly Gly Val Gly Lys Thr Thr
                 5                  10                  15

Cys Ser Cys Ser Leu Ala Ala Lys Leu Ile Asp Ser Leu Asp Phe
                 20                  25                  30

Asp Val Val Val Phe Asp Thr Ala Pro Thr Gly His Thr Leu Arg
                 35                  40                  45

Leu Leu Gln Phe
            49

(2) INFORMATION FOR SEQ ID NO: 16:

(i) SEQUENCE CHARACTERISTICS:
        (A) LENGTH: 49
        (B) TYPE: amino acid
        (C) STRANDEDNESS:
        (D) TOPOLOGY: linear (ii) MOLECULE TYPE: Protein (iii) HYPOTHETICAL: No (iv) ANTI-SENSE: No (v) SEQUENCE DESCRIPTION: SEQ ID NO:16:

```
Lys Thr Ile Phe Val Gly Gly Lys Gly Val Gly Lys Thr Thr
                  5                  10                 15

Cys Ser Cys Ser Leu Ala Val Arg Leu Val Lys Gly Met Asn Phe
                20                  25                  30

Ser Val Val Val Phe Asp Thr Ala Pro Thr Gly His Thr Leu Arg
                35                  40                  45

Leu Leu Asn Phe
            49
```